US008381961B2

(12) United States Patent
Holsten et al.

(10) Patent No.: US 8,381,961 B2
(45) Date of Patent: Feb. 26, 2013

(54) SURGICAL STAPLING APPARATUS INCLUDING STAPLE WITH PLATE (75) Inventors: Henry E. Holsten, Covington, GA (US); Kenneth Blier, Cheshire, CT (US)

(73) Assignee: Covidien LP, Mansfield, MA (US)

( * ) Notice: Subject to any disclaimer, the term of this patent is extended or adjusted under 35 U.S.C. 154(b) by 523 days.

(21) Appl. No.: 12/631,060

(22) Filed: Dec. 4, 2009

(65) Prior Publication Data

US 2010/0217314 A1 Aug. 26, 2010

Related U.S. Application Data (60) Provisional application No. 61/144,487, filed on Jan. 14, 2009.

(51) Int. Cl.
*A61B 17/064* (2006.01)
(52) U.S. Cl. ........ 227/175.1; 227/19; 606/219; 411/457
(58) Field of Classification Search .... 227/175.1–182.1, 227/19; 606/219, 220; 411/457
See application file for complete search history.

(56) References Cited

U.S. PATENT DOCUMENTS

| | | | | |
|---|---|---|---|---|
| 389,660 | A * | 9/1888 | Mandel et al. | 24/703.4 |
| 2,897,561 | A * | 8/1959 | Megibow | 24/95 |
| 3,357,296 | A * | 12/1967 | Lefever | 411/469 |
| 3,744,495 | A * | 7/1973 | Johnson | 606/142 |
| 4,129,059 | A * | 12/1978 | Van Eck | 411/475 |
| 4,434,796 | A * | 3/1984 | Karapetian et al. | 606/75 |
| 4,532,927 | A * | 8/1985 | Miksza, Jr. | 606/220 |
| 4,534,352 | A | 8/1985 | Korthoff | |
| 4,573,469 | A | 3/1986 | Golden et al. | |
| 4,610,250 | A * | 9/1986 | Green | 606/220 |
| 4,627,437 | A * | 12/1986 | Bedi et al. | 606/220 |
| 4,646,741 | A | 3/1987 | Smith | |
| 4,667,674 | A | 5/1987 | Korthoff et al. | |
| 4,671,280 | A | 6/1987 | Dorband et al. | |
| 4,693,248 | A | 9/1987 | Failla | |
| 4,741,336 | A | 5/1988 | Failla et al. | |
| 4,805,617 | A | 2/1989 | Bedi et al. | |
| 4,890,613 | A | 1/1990 | Golden et al. | |
| 4,932,960 | A | 6/1990 | Green et al. | |
| 5,258,009 | A * | 11/1993 | Conners | 606/219 |
| 5,258,012 | A | 11/1993 | Luscombe et al. | |
| 5,282,829 | A | 2/1994 | Hermes | |
| 5,292,334 | A | 3/1994 | Howansky | |
| 5,293,881 | A | 3/1994 | Green et al. | |
| 5,350,400 | A * | 9/1994 | Esposito et al. | 606/219 |
| 5,425,489 | A * | 6/1995 | Shichman et al. | 227/108 |
| 5,439,479 | A * | 8/1995 | Shichman et al. | 606/220 |
| 5,584,856 | A * | 12/1996 | Jameel et al. | 606/220 |
| 5,620,452 | A * | 4/1997 | Yoon | 606/151 |
| 5,843,126 | A * | 12/1998 | Jameel | 606/220 |
| RE37,814 | E | 8/2002 | Allgeyer | |
| 6,497,707 | B1 | 12/2002 | Bowman et al. | |
| 6,503,259 | B2 | 1/2003 | Huxel et al. | |
| 7,001,411 | B1 | 2/2006 | Dean | |
| 7,033,378 | B2 | 4/2006 | Smith et al. | |
| 2006/0235469 | A1 | 10/2006 | Viola | |
| 2007/0010854 | A1 | 1/2007 | Cummins | |
| 2010/0137904 | A1* | 6/2010 | Wenchell | 606/220 |
| 2010/0217314 | A1* | 8/2010 | Holsten et al. | 606/220 |
| 2011/0087276 | A1* | 4/2011 | Bedi et al. | 606/219 |

* cited by examiner

*Primary Examiner* — Lindsay Low (57) ABSTRACT

A fastener system includes an open loop member and a receiving plate. The open loop member has first and second legs and a base. Each leg defines a longitudinal axis therethrough. The receiving plate has a body including a pair of spaced apart channels. The body defines a longitudinal axis therethrough. Each channel is positioned to receive a portion of one of the first or second legs.

19 Claims, 8 Drawing Sheets

SURGICAL STAPLING APPARATUS INCLUDING STAPLE WITH PLATE

This application claims priority from provisional application Ser. No. 61/144,487 filed Jan. 14, 2009, the entire contents of which are incorporated herein by reference.

BACKGROUND

1. Technical Field

This application relates, in general, to surgical stapling apparatus, and more particularly, to atraumatic surgical fasteners for use therewith.

2. Background of Related Art

Many varieties of surgical fastening apparatus are known in the art, some of which are specifically adapted for use in various surgical procedures including, but not limited to, end-to-end anastomosis, circular end-to-end anastomosis, open gastrointestinal anastomosis, endoscopic gastrointestinal anastomosis, and transverse anastomosis. Suitable examples of apparatus which may be used during the course these procedures can be seen in U.S. Pat. Nos. 5,915,616; 6,202,914; 5,865,361; and 5,964,394.

In general, a surgical fastening apparatus will include an anvil that is approximated to a fastener cartridge (or fastener cartridge approximated to an anvil) during use. The anvil includes depressions that are aligned with, and/or are in registration with, slots defined in the cartridge through which the fasteners will emerge, to effectuate formation. The fastener cartridge typically has one or more rows of fasteners disposed laterally or radially of a channel. The channel can be configured to accommodate a knife, or other such cutting element, such that tissue can be simultaneously cut and joined together. Depending upon the particular surgical fastening apparatus, the rows of fasteners may be arranged in a linear or non-linear, e.g. circular, semi-circular, or otherwise arcuate configuration.

Various types of surgical fasteners are well known in the art, including but not limited to unitary fasteners and two-part fasteners. Unitary fasteners generally include a pair of legs adapted to penetrate tissue and which extend from a backspan. In use, subsequent to formation, some of the unitary fasteners have a "B" configuration. Typically, the two-part fastener includes legs that are barbed and extend from a backspan which are engaged and locked into a separate retainer piece that is usually located in the anvil. In use, the two-part fastener is pressed into the tissue so that the barbs penetrate the tissue and emerge from the other side where they are then locked into the retainer piece. The retainers prevent the two-part fastener from dislodging from the tissue. The two-part fasteners are not intended to be unlocked or removable. These fasteners are generally made of a bioabsorbable material.

During each of the aforementioned surgical procedures, the tissue is initially gripped or clamped such that individual fasteners can be ejected from the cartridge, through the slots, and forced through the clamped tissue. Thereafter, the fasteners are formed by driving them into the depressions formed on the anvil (or into locking retainers).

In staplers of the general type described above, it is conventional to provide separate anvil slots at each staple forming location. This makes it necessary to maintain relatively stringent alignment between the staple holding assembly and the anvil to assure that the staples enter the anvil slots correctly for proper clinching. The importance of maintaining good alignment between the relatively movable staple holding assembly and anvil assembly may contribute to the complexity of the instrument and to the cost of manufacturing and maintaining it. It is important that every staple be formed properly since an incompletely or improperly formed staple may leave a gap in a wound closure.

SUMMARY

The present invention relates in one aspect to a surgical stapling apparatus including a housing having an actuator, an actuation mechanism operatively coupled to the actuator, and a tool assembly operatively connected to the actuation mechanism. The tool assembly has a cartridge assembly and an anvil assembly relatively movably to clamp tissue therebetween. The tool assembly accommodates a fastener system. The surgical fastener system includes an open loop member and a receiving plate. The open loop member has first and second legs and a base (backspan). Each leg defines a longitudinal axis therethrough and is configured and dimensioned to penetrate tissue.

In one aspect, the receiving plate includes a body having a pair of spaced apart channels. The body defines a longitudinal axis therethrough. Each channel is positioned to receive at least a portion of one of the first or second legs.

Preferably, each channel is configured and dimensioned to direct at least a portion of at least one of the legs at least partially therethrough. In order to accommodate at least a portion of one of the legs, each channel preferably has a cover disposed over at least a portion thereof. Each channel is preferably disposed at an angle substantially perpendicular to the longitudinal axis of each of the legs and preferably at least partially angled away from the longitudinal axis of the body.

The actuator is movable to effect advancement of the actuation mechanism. The advancement of the actuation mechanism effects the ejection of the open loop member and the forming of a portion of the legs into a portion of the channels of the receiving plate. The receiving plate and the open loop fastener preferably form a closed box-like configuration upon engagement with each other.

The present disclosure also provides in another aspect a two part surgical fastener comprising a staple and a receiving plate, the staple having a backspan and first and second legs extending therefrom. The legs have distal tips configured to penetrate tissue. The receiving plate has first and second channels to receive the distal tip of the respective staple leg and direct the staple leg inwardly toward an opposing staple leg to bend the legs inwardly to form a bent staple leg portion. A cover extends from the receiving plate to cover a portion of the bent staple leg portion.

A first cover can be provided disposed over at least a portion of the first channel and/or a second cover can be provided disposed over at least a portion of the second channel.

In another aspect, the present disclosure provides a surgical fastener system comprising an open loop member having first and second legs and a base, each leg defining a longitudinal axis therethrough and configured and dimensioned to penetrate tissue. A receiving plate has a body defining a longitudinal axis therethrough, the body including first and second spaced apart channels, each channel positioned to receive at least a portion of one of the first or second legs. Each channel is disposed at an angle substantially perpendicular to the longitudinal axis of each of the legs and at least partially angled away with respect to the longitudinal axis of the body.

In one embodiment, the receiving plate has a length greater than a length of the open loop member. In one embodiment, the receiving plate has a width greater than a width of the open loop member. Preferably, the receiving plate and the open loop member form a closed box-like configuration upon engagement with each other.

The system can include a cover disposed over at least a portion of the first channel and a second cover disposed over at least a portion of the second channel.

In a preferred embodiment, the first and second channels are formed on a first surface of the retaining plate, and third and fourth channels are formed on a second opposing surface.

Preferably a cover extends from the second surface of the retaining plate.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION OF EMBODIMENTS

Particular embodiments of the present disclosure will be described herein with reference to the accompanying drawings. As shown in the drawings and as described throughout the following description, and as is traditional when referring to relative positioning on an object, the term "proximal" refers to the end of the apparatus that is closer to the user and the term "distal" refers to the end of the apparatus that is further from the user.

Figure 1:
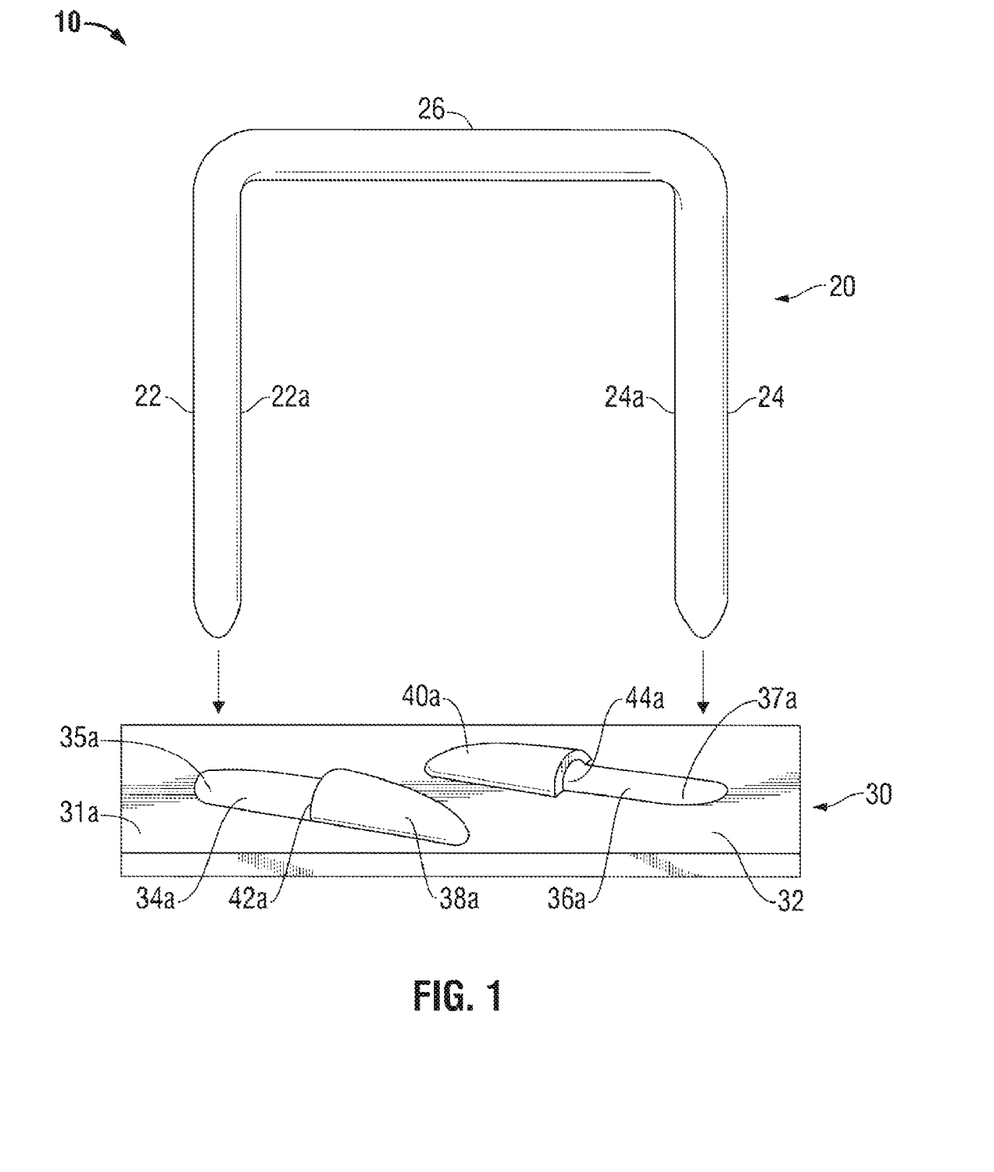
FIG. 1 is a side view of the fastener system accordance with the present disclosure prior to engagement of the staple legs with the plate.
Figure 2:
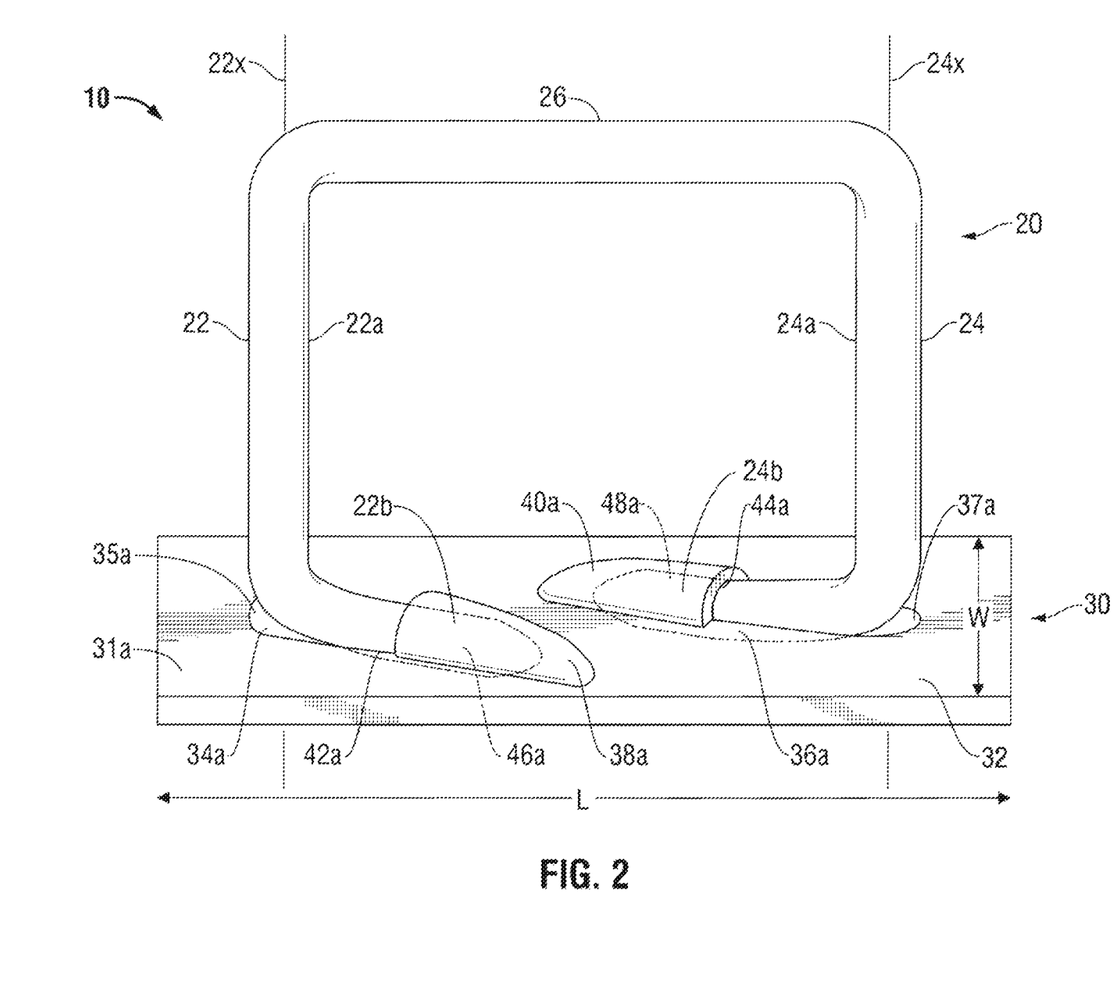
FIG. 2 is a top perspective view of the fastener system in accordance with the present disclosure showing engagement of the staple legs with the plate.
Figure 2A:
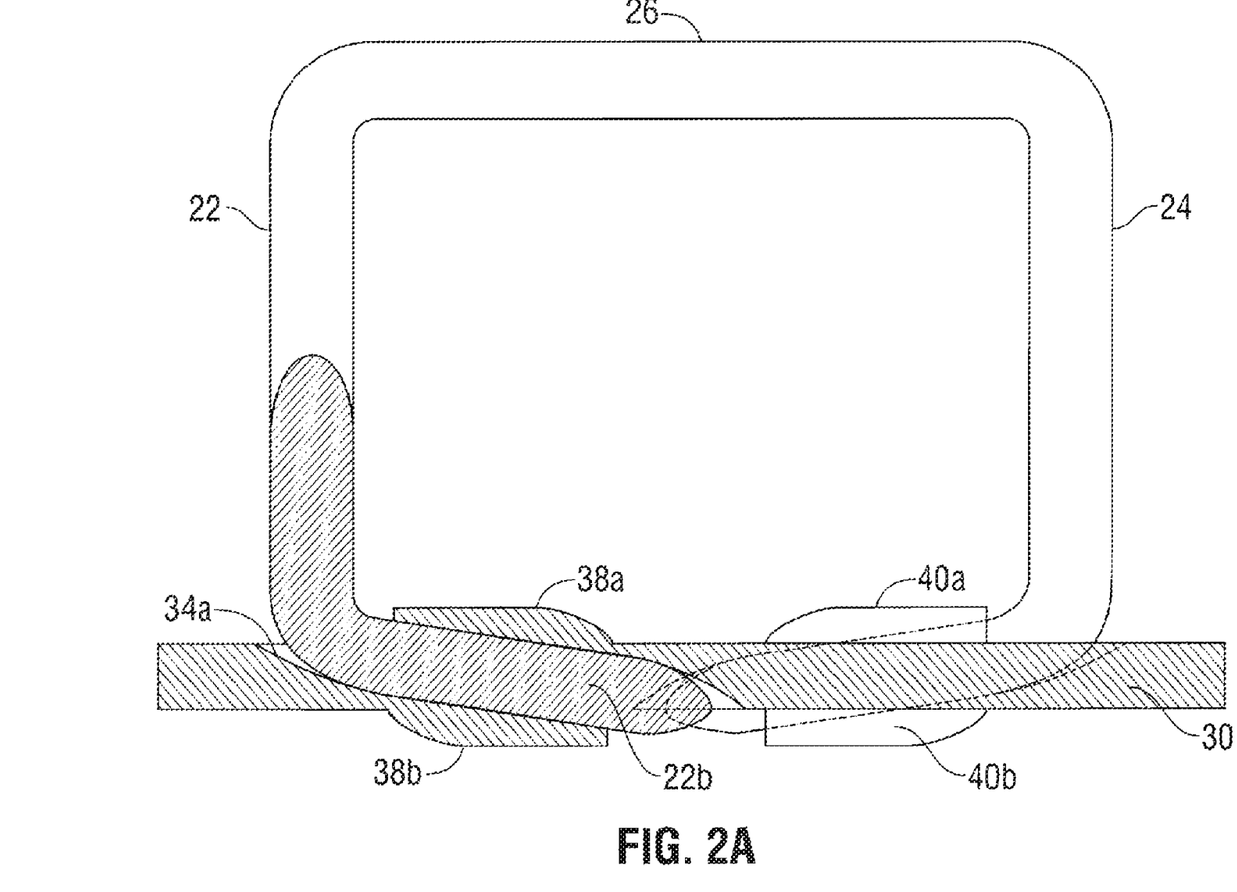
FIG. 2A is a side view in partial cross-section of the fastener system of FIG. 1.
Figure 3:
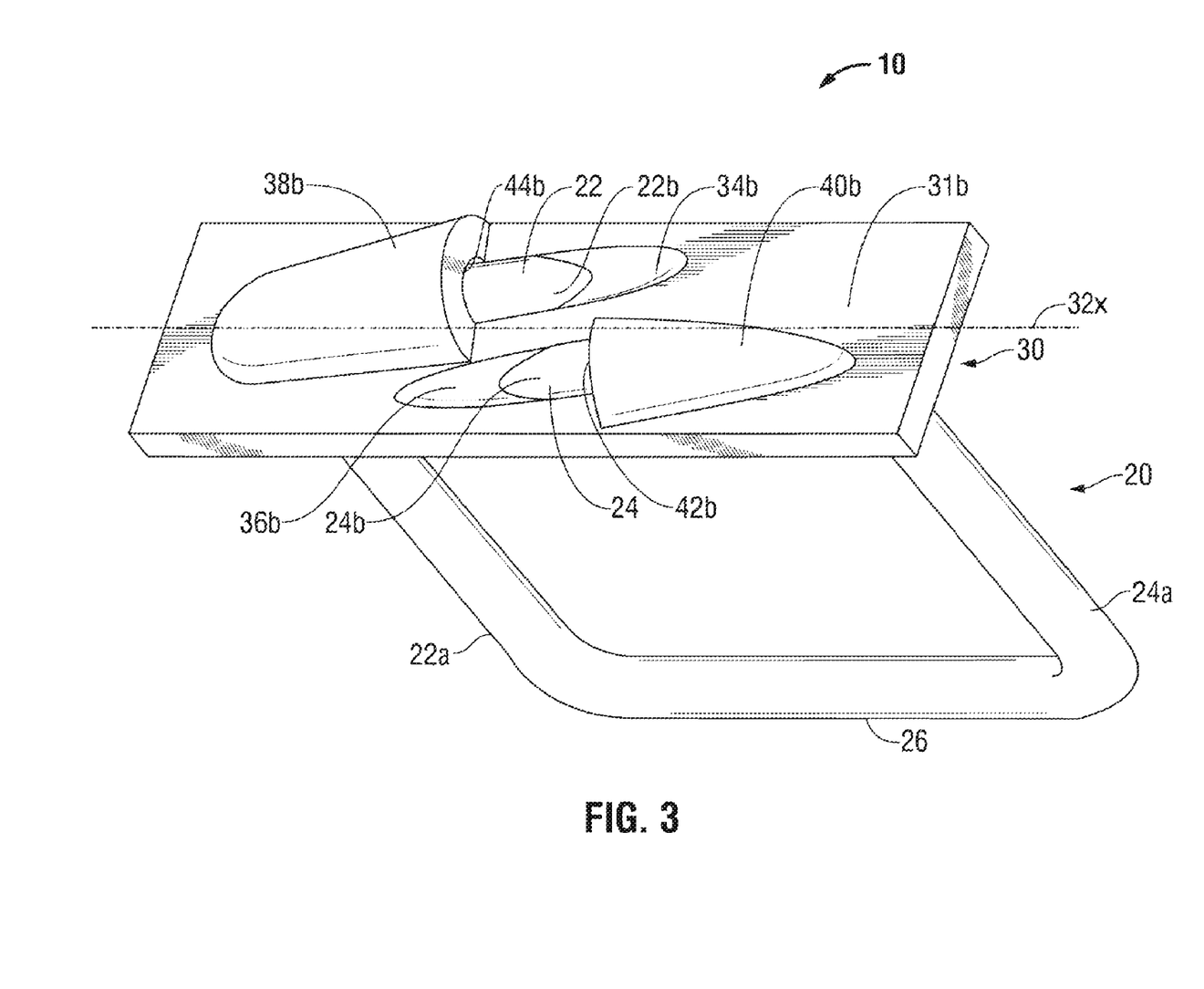
FIG. 3 is a bottom perspective view of the fastener system of FIG. 2.
Figure 4:
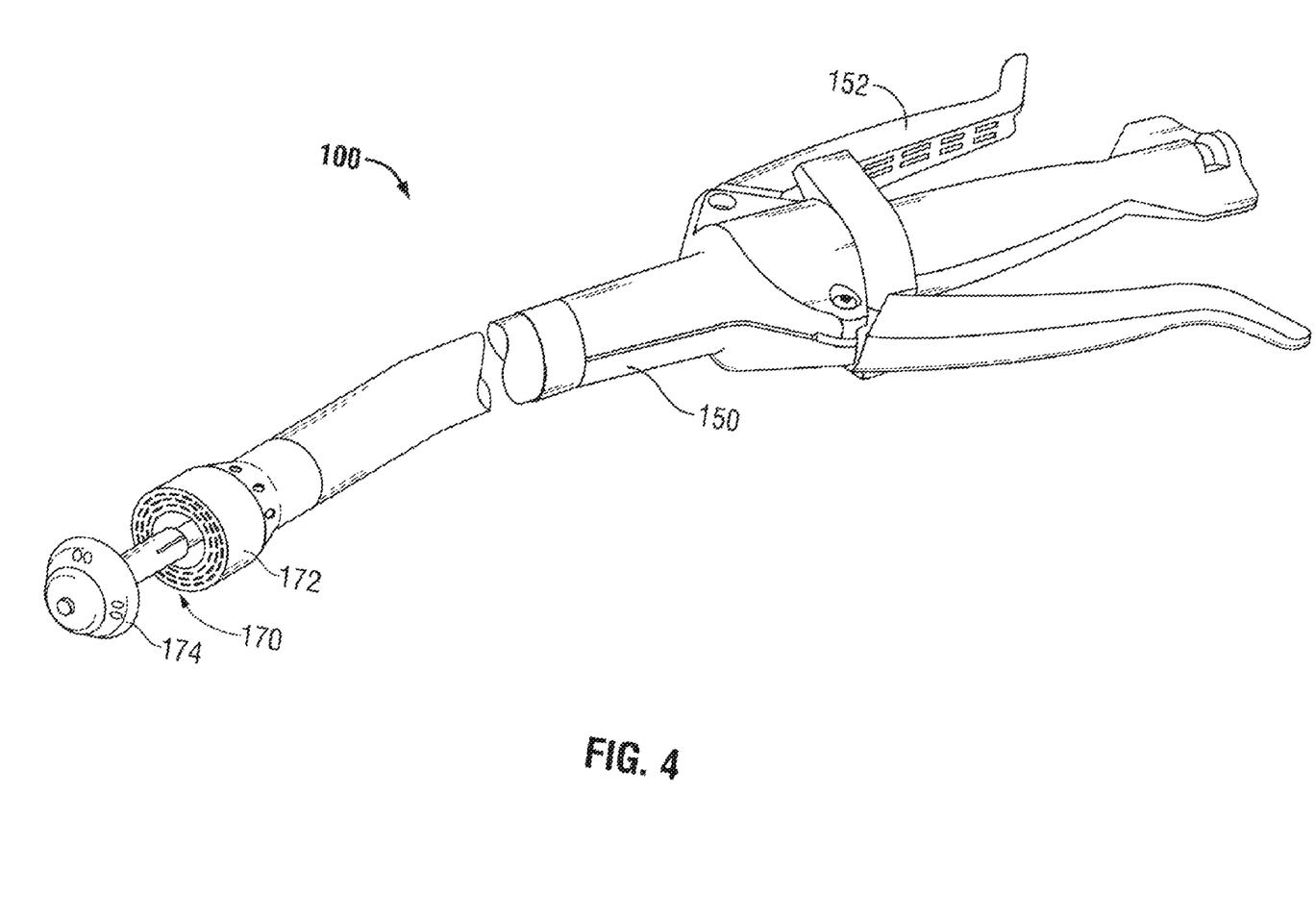
FIG. 4 is a perspective view of one embodiment of a surgical stapling apparatus having the fastener system of FIG. 1 in accordance with the present disclosure.
Figure 5:
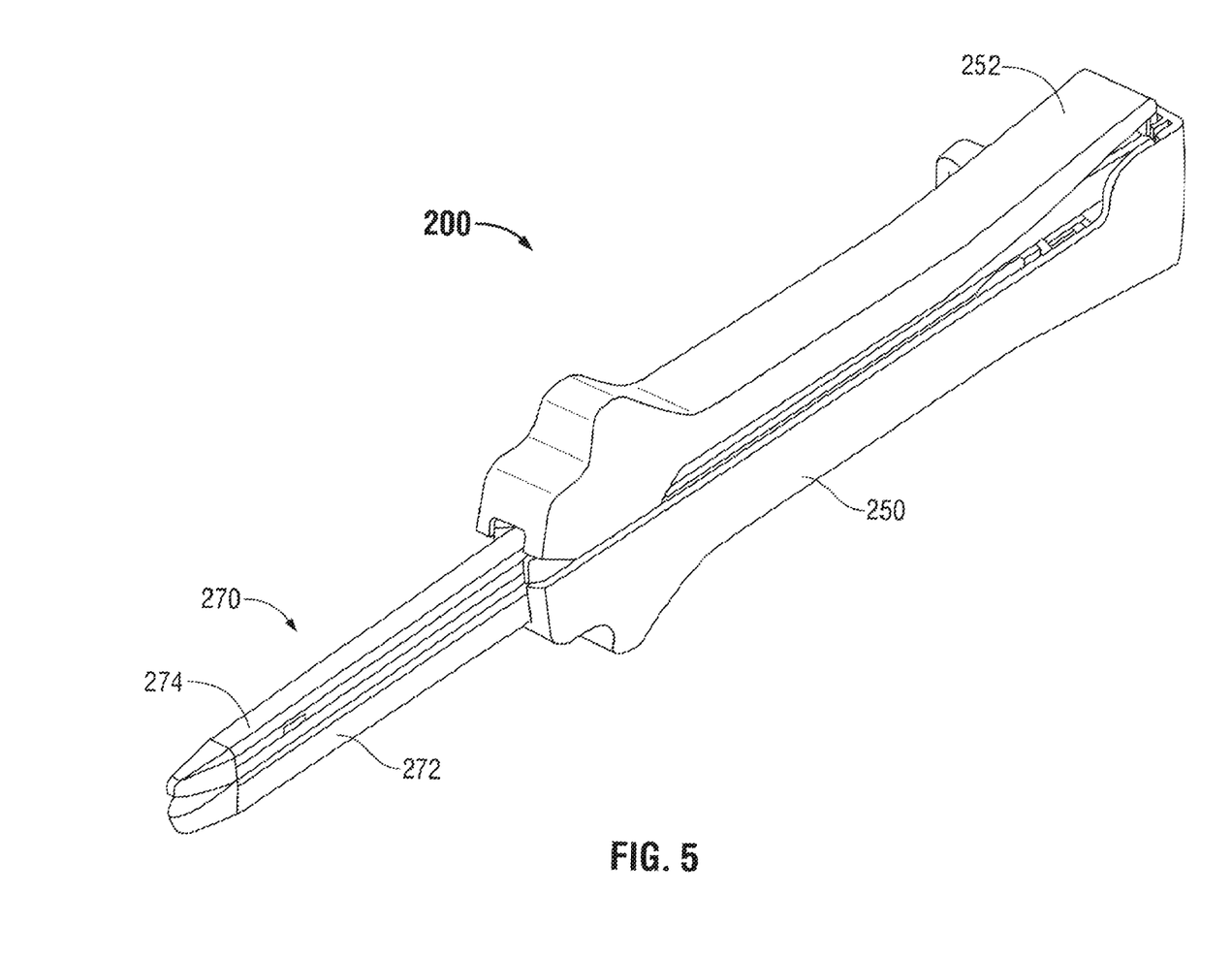
FIG. 5 is a perspective view of another embodiment of a surgical stapling apparatus having the fastener system of FIG. 1 in accordance with the present disclosure.
Figure 6:
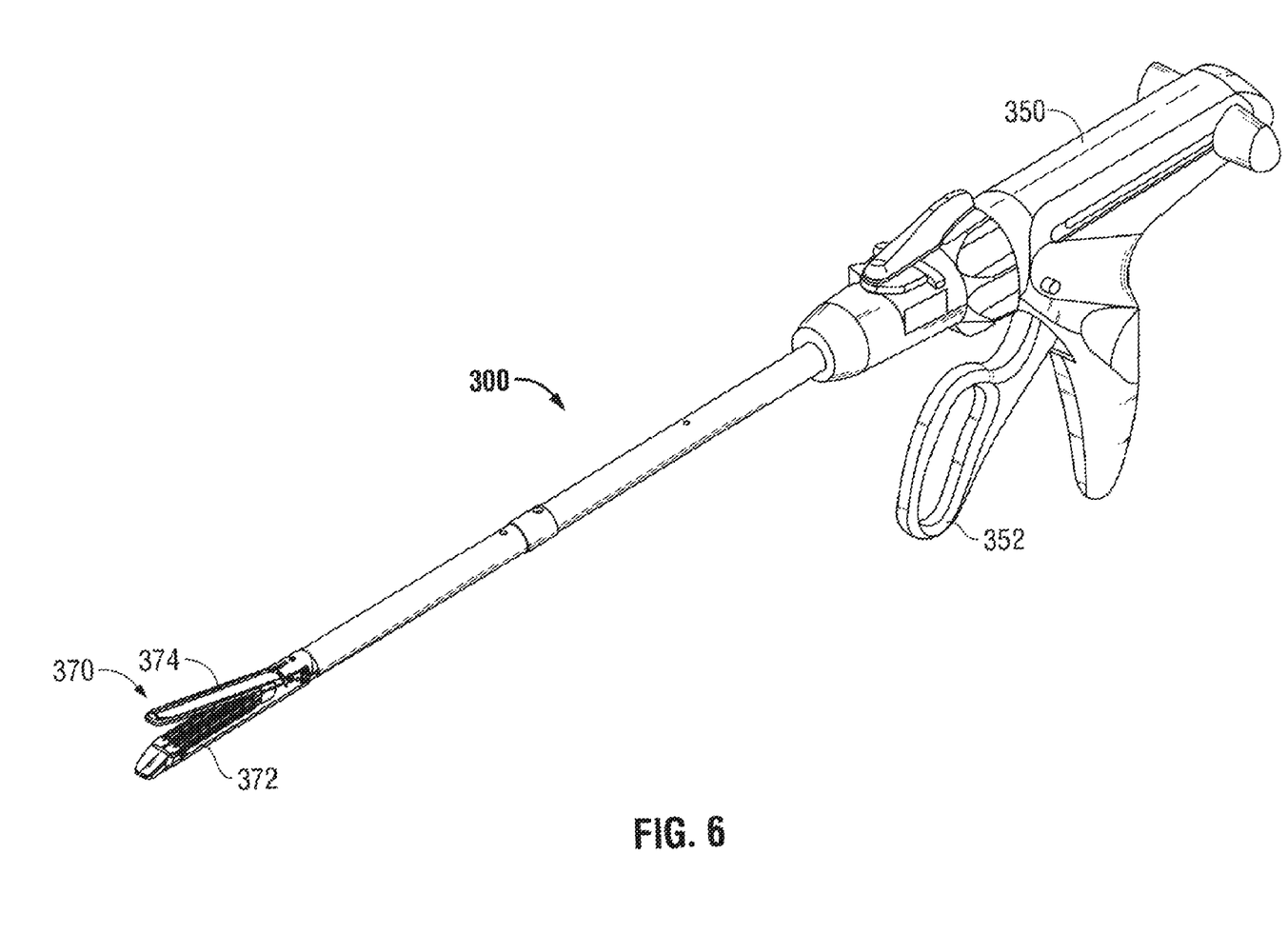
FIG. 6 is a perspective view of a further embodiment of a surgical stapling apparatus having the fastener system of FIG. 1 in accordance with the present disclosure.

Referring now to the drawings, in which like reference numerals identify identical or substantially similar parts throughout the several views, FIGS. 1-3 illustrate a surgical fastener system 10. In accordance with the present disclosure, the fastener system 10 includes an open loop member 20 and a receiving plate 30. The receiving plate 30 and the open loop member 20 form a closed box-like configuration upon engagement with each other as shown in FIGS. 1 and 2. The open loop member 20 is in the form of a staple including a first leg 22 and a second leg 24 extending from a base (backspan) 26. Each leg 22, 24 defines a longitudinal axis 22x, 24x through the unformed portion 22a, 24a, thereof. Each leg 22, 24 is configured and dimensioned to penetrate tissue, and has a penetrating distal tip. Each leg 22, 24 is preferably substantially perpendicular to a longitudinal axis of the base 26; however, the legs can also be positioned at other angles to the base 26. In the unformed position, each leg is preferably substantially straight and the legs 22, 24 are preferably substantially parallel to one another as shown in FIG. 1.

The receiving plate 30 includes a body 32 having a longitudinal axis 32x. The body 32 has a width W wider than the width of the open loop member 20 and a length L longer than the length of the backspan 26. The body 32 includes a top (upper) surface 31a and a bottom (lower) surface 31b. The top surface 31a has first channel 34a and a second channel 36a. The first and second channels 34a, 36a are disposed in spaced apart relation relative to each other. The channels 34a, 36a are partially disposed within the body 32 of the receiving plate 30 and in the illustrated embodiment have a substantially parabolic shape. Each channel 34a, 36a is positioned to receive at least a portion 22b, 24b of one of the first or second legs 22, 24. Preferably, each channel 34a, 36a is disposed at an angle substantially perpendicular to the longitudinal axes 22x, 24x of first and second legs 22, 24 and preferably at least partially angled with respect to the longitudinal axis 32x of the body 32. The channels 34a, 36a are configured and dimensioned to direct at least a portion of at least one of the legs 22, 24 at least partially through the channel as the legs contact the edge of the respective channel and are bent inward toward the opposing leg. The channels 34a, 36a are also configured and dimensioned to accommodate at least a portion 22b, 24b of one of the legs 22, 24 when it is in the formed (bent) configuration.

As shown in FIG. 1, a first cover 38a extending upwardly from the top surface 31a of body 32 (as viewed in the orientation of FIG. 1) is disposed over at least a portion of the first channel 34a. A second cover 40a extending upwardly from the top surface 31a of body 32 is disposed over at least a portion of the second channel 36a. Each cover 38a, 40a can be disposed at the end of its respective channel 34a, 36a. Each cover 38a, 40a illustratively has a substantially conical shape, although other shapes are contemplated. The covers can be integrally formed with the base or separate components attached thereto. Each cover has an opening adjacent the top surface 31a which extends to the bottom surface 31b. Bottom surface 31b (FIG. 3) has channels 34b, 36b and covers 38b, 40b (similar to covers 38a, 40a) disposed over at least a portion thereof. The legs 22, 24 extend through the covers 38b, 40b, emerging at openings 44b, 42b, and into channels 34b, 36b, respectively. Like channels, 34a, 36a, each channel 34b, 36b is preferably disposed at an angle substantially perpendicular to the longitudinal axes 22x, 24x of first and second legs 22, 24 and preferably at least partially angled away from the longitudinal axis 32x of the body 32. The channels 34b, 36b are configured and dimensioned to accommodate at least a portion 22b, 24b of one of the legs 22, 24.

Figure 7:
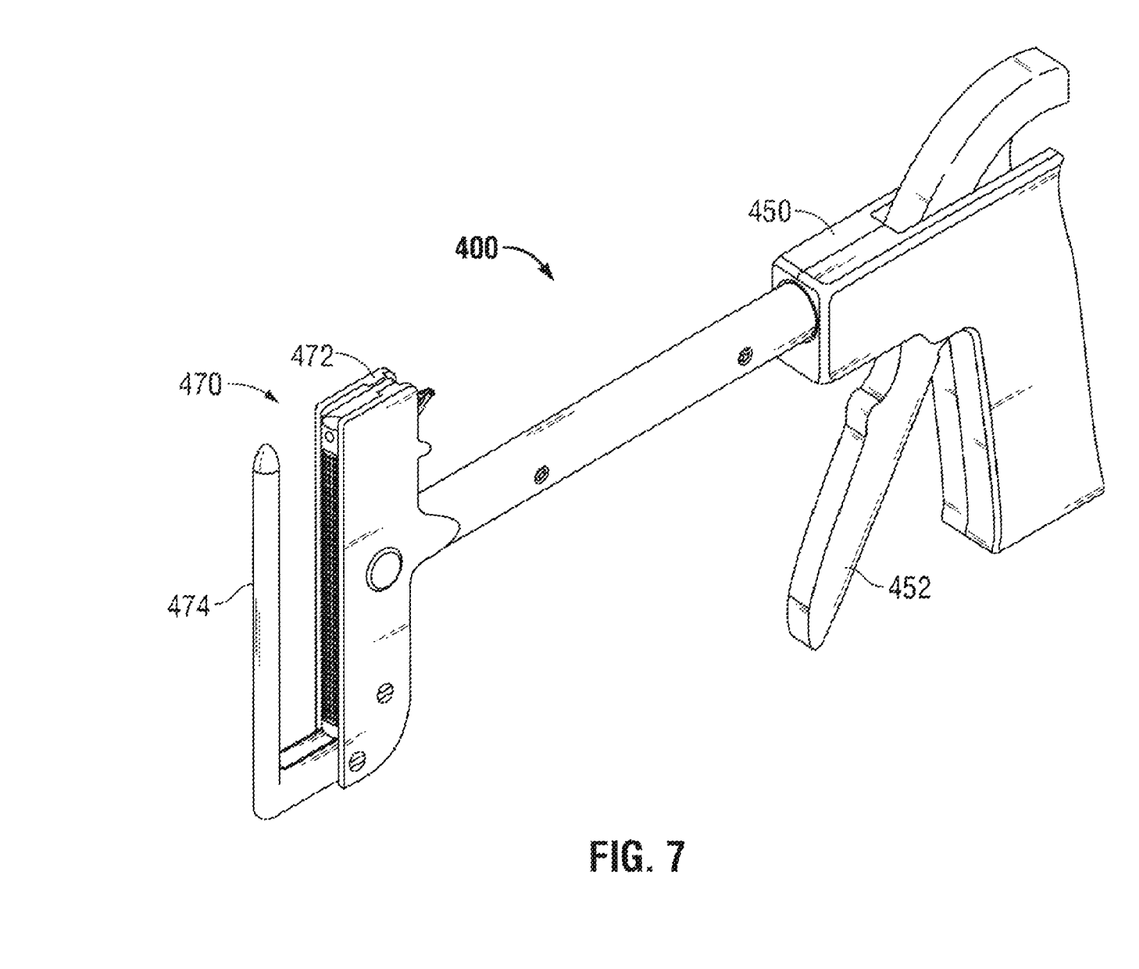
FIG. 7 is a perspective view of yet another embodiment of a surgical stapling apparatus having the fastener system of FIG. 1 in accordance with the present disclosure.

As shown in FIGS. 4-7, it is contemplated that the disclosed fastener system can be configured for use by way of example with a circular stapling apparatus 100 (FIG. 4), linear stapling apparatus including open 200 (FIG. 5) and endoscopic 300 (FIG. 6), as well as a transverse stapling apparatus 400 (FIG. 7). Typically, each of these devices include a housing 150, 250, 350, 450 having an actuator 152, 252, 352, 452, an actuation mechanism operatively coupled to the actuator 152, 252, 352, 452 and a tool assembly 170, 270, 370, 470. The tool assembly 170, 270, 370, 470 is operatively coupled to the actuation mechanism. The tool assembly 170, 270, 370, 470 has a cartridge assembly 172, 272, 372, 472 and an anvil assembly 174, 274, 374, 474 movably mounted in relation to the cartridge assembly 172, 272, 372, 472. The tool assembly 170, 270, 370, 470 accommodates the fastener system 10 described above. In particular, a plurality of open loop members 20 are disposed in the cartridge assembly 172, 272, 372, 472. A plurality of receiving plates 30 are disposed in the anvil assembly 174, 274, 374, 474 opposite a respective loop member 20. A circular stapling apparatus is disclosed, for example, in U.S. Pat. No. 5,915,616, and 7,303, 106 the entire contents of which are incorporated herein by reference. An open stapling apparatus is disclosed, for example, in U.S. Pat. No. 6,202,914 and 7,055,730, the entire contents of which are incorporated herein by reference. An endoscopic stapling apparatus is disclosed, for example, in U.S. Pat. Nos. 5,865,361, the entire contents of which are incorporated herein by reference. A transverse stapling apparatus is disclosed, for example, in U.S. Pat. No. 6,817,508 the entire contents of which are incorporated herein by reference. The fastener system of the present disclosure can be also used in other apparatus.

The actuator 152, 252, 352, 452 is movable to effect advancement of the actuation mechanism which effects the ejection of the open loop members 20 from the cartridge assembly 172, 272, 372, 472 and the forming of at least a portion of at least one of the legs 22, 24 into at least a portion of at least one of the channels 34, 36 of the receiving plate 30. As such, in use, upon actuation of the actuator 152, 252, 352, 452, the actuation mechanism causes firing of the open loop members 20 so that they penetrate tissue and form in the corresponding receiving plate 30, facilitating an atraumatic wound closure.

More specifically, the loop members 20 are positioned in the cartridge with the legs 22, 24 in a substantially straight configuration, and preferably substantially parallel to one another (see FIG. 1). Upon actuation, the open loop members 20 are fired (advanced) from the cartridge, and each of the legs 22, 24 penetrates tissue, and then engages the respective channel 34a, 36a of the receiving plate 30 at initial contact regions 35a, 37a at the edge of the respective channel. Each channel 34a, 36a correspondingly causes the respective leg 22, 24 to form (bend) inwardly along the respective channel 34a, 36a in a direction toward the opposing leg. The distal end of each leg 22, 24, translates inwardly along the channel and into a respective opening 42a, 44a at the receiving end of each cover 38a, 40a and into a respective space 46a, 48a (FIG. 2) defined in the interior of each cover 38a, 40a. This space extends into covers 38b, 40b on bottom surface 31b. As formation continues, depending on the extent of formation and/or the length of the legs, the distal end of the legs 22, 24 would pass through respective openings 42b, 44b, in covers 38b, 40b, and into respective channels 34b, 36b. As such, a portion of each leg 22, 24, an unformed portion 22a, 24a, remains unformed. Similarly, a portion of each leg 22, 24, a formed portion 22b, 24b, is formed into the receiving plate 30, causing the formation of a completed surgical fastener system 10.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Thus the scope of the embodiments should be determined by the appended claims and their legal equivalents, rather than by the examples given.

What is claimed is:

1. A surgical fastener system comprising:
an open loop member having first and second legs and a base, each leg defining a longitudinal axis therethrough, each leg configured and dimensioned to penetrate tissue; and
a receiving plate, the receiving plate having a body, the body defining a longitudinal axis therethrough, the body including first and second spaced apart channels, each channel positioned to receive at least a portion of one of the first or second legs, each channel disposed at an angle substantially perpendicular to the longitudinal axis of each of the legs and at least partially angled away with respect to the longitudinal axis of the body,
wherein the first and second spaced apart channels are formed on a first surface of the receiving plate, and the receiving plate further includes third and fourth channels formed on an opposing surface of the plate.

2. The fastener system according to claim 1, wherein the receiving plate has a length greater than a length of the open loop member.

3. The fastener system according to claim 1, wherein the receiving plate has a width greater than a width of the open loop member.

4. The fastener system according to claim 1, wherein the receiving plate and the open loop member form a closed box-like configuration upon engagement with each other.

5. The fastener system according to claim 1, wherein at least one of the channels is configured and dimensioned to direct at least a portion of at least one of the legs at least partially therealong.

6. The fastener system according to claim 1, wherein at least one of the channels is configured and dimensioned to accommodate at least a portion of one of the legs.

7. The fastener system according to claim 1, wherein at least one of the channels has a substantially parabolic shape.

8. The fastener system according to claim 1, further comprising a cover, the cover disposed over at least a portion of the first channel.

9. The fastener system according to claim 8, wherein the cover has an opening to receive a portion of one of the legs.

10. The fastener system according to claim 8, wherein the cover has a substantially conical shape.

11. The fastener system according to claim 8, further comprising a second cover disposed over at least a portion of the second channel.

12. The fastener system according to claim 1, further comprising a cover disposed over at least a portion of the third channel.

13. A surgical stapling apparatus comprising:
a housing having an actuator;
an actuation mechanism operatively coupled to the actuator; and
a tool assembly operatively coupled to the actuation mechanism, the tool assembly having a cartridge assembly and an anvil assembly relatively movable to clamp tissue therebetween, the tool assembly accommodating a fastener system, the fastener system including:
an open loop member having first and second legs and a base, each leg defining a longitudinal axis therethrough, each leg configured and dimensioned to penetrate tissue; and
a receiving plate, the receiving plate having a body, the body defining a longitudinal axis therethrough, the body including a first pair of spaced apart channels formed on a first surface of the receiving plate and at least one other channel formed on a second surface of the receiving plate the first surface being opposite to the second surface, each channel of the first pair of spaced apart channels positioned to receive at least a portion of one of the first or second legs, each channel of the first pair of spaced apart channels disposed at an angle substantially perpendicular to the longitudinal axis of each of the legs and at least partially angled with respect to the longitudinal axis of the body;

wherein the actuator is movable to effect advancement of the actuation mechanism, the advancement of the actuation mechanism effecting ejection of the open loop member and the forming of at least a portion of at least one of the legs into at least a portion of at least one of the channels of the receiving plate.

14. The fastener system according to claim 13, further comprising a cover, the cover disposed over at least a portion of the first channel.

15. The fastener system according to claim 14, further comprising a second cover disposed over at least a portion of the second channel.

16. The fastener system according to claim 13, wherein at least one of the channels is configured and dimensioned to direct at least a portion of at least one of the legs at least partially therealong.

17. The fastener system of claim 13, wherein the at least one other channel formed on a second surface of the receiving plate includes a plurality of channels.

18. A two part surgical fastener comprising a staple and a receiving plate, the staple having a backspan and first and second legs extending therefrom, the legs having distal tips to penetrate tissue, the receiving plate having first and second channels to receive the distal tip of the respective staple leg and direct the staple leg inwardly toward an opposing staple leg to bend the legs inwardly to form a bent staple leg portion, and a cover extending from the receiving plate to cover a portion of the bent staple leg portion,
wherein the first and second channels are formed on a first surface of the receiving plate, the receiving plate further having a second opposing surface with a pair of channels formed therein.

19. The fastener of claim 18, further comprising a cover extending from the second surface of the receiving plate.

* * * * *